United States Patent [19]

Kuntz

[11] Patent Number: 4,581,023
[45] Date of Patent: Apr. 8, 1986

[54] HYPODERMIC SYRINGE ASSEMBLY

[76] Inventor: David H. Kuntz, 11810 Bel Terrace, Los Angeles, Calif. 90049

[21] Appl. No.: 700,903

[22] Filed: Feb. 12, 1985

[51] Int. Cl.$^4$ .......................................... A61M 5/245
[52] U.S. Cl. ................................................. 604/234
[58] Field of Search ................ 604/234, 233, 218, 232

[56] References Cited

U.S. PATENT DOCUMENTS

| | | | |
|---|---|---|---|
| 2,871,858 | 2/1959 | Dann et al. | 604/233 |
| 3,811,441 | 5/1974 | Sarnoff | 604/234 |
| 4,011,868 | 3/1977 | Friend | 604/218 |
| 4,221,218 | 9/1980 | Pfleger | 604/218 |

Primary Examiner—John D. Yasko
Attorney, Agent, or Firm—Philip D. Junkins

[57] ABSTRACT

A one-time-use, disposable hypodermic syringe assembly in pre-packaged, pre-injection arrangement is provided and comprises: a plastic syringe barrel with a hypodermic needle mounted in its forward injection delivery end, the injection point of such needle projecting outwardly and forwardly of the barrel and the butt end of such needle projecting rearwardly within the barrel; a medicament-filled ampule positioned within the syringe barrel and having a pierceable diaphragm closure at its forward end and a piston-type stopper at its rearward end; and a plunger removably mounted on the outside of the syringe barrel and providing means while so mounted for locking the ampule, at its diaphragm closure end, out of piercing contact with the rearwardly extending butt end of the hypodermic needle, the plunger having means for connecting with the piston-type stopper of the ampule for use in moving the ampule, after removal of the plunger from its ampule-locking position on the syringe barrel, forwardly to effect piercing of the diaphragm by the butt end of the needle and thereafter in moving the piston-type stopper within the ampule to express medicament out of the ampule and through the needle for injection purposes.

11 Claims, 7 Drawing Figures

HYPODERMIC SYRINGE ASSEMBLY

BACKGROUND OF THE INVENTION

The present invention relates to an improved hypodermic syringe assembly which is designed to be relatively simple and inexpensive to manufacture and package, so as to be disposable after one-time use, and which is particularly suited to being packaged and sold with a medicament-filled ampule seated in the syringe assembly ready for use.

Numerous disposable hypodermic syringes have been proposed over the years which have a fixed needle or cannula at the forward end of the syringe barrel and a plunger inserted into the syringe barrel through the rearward end thereof with the plunger being movable within the barrel to aspirate medicament into the syringe through the needle and to expel medicament out of the syringe through the needle for making hypodermic injections. Further, both reusable and disposable hypodermic syringes have been designed whereby the syringe barrel may be either side-loaded or end-loaded with a medicament-filled ampule having a stopper or diaphragm which is pierceable by the sharpened butt end of the needle mounted at the forward end of the syringe barrel. In such ampule-syringe assemblies the plunger either moves the ampule with respect to a stopper to expel medicament from the ampule or moves a stopper with respect to the ampule to expel the medicament.

There remains a need for a pre-packaged, pre-sterilized, disposable hypodermic syringe assembly with a medicament-filled ampule seated within the syringe barrel substantially ready-for-use, but with the syringe protected against accidental expulsion of the medicament while the syringe is in its packaging.

SUMMARY OF THE INVENTION

The present invention relates to a one-time-use, disposable hypodermic syringe assembly which is pre-packaged with a medicament-filled ampule situate within the syringe barrel in pre-injection position out of fluid communication with the hypodermic needle of the syringe. In its pre-packaged state, the syringe plunger is positioned along the outside of the syringe barrel and mounted thereon in a manner such that the medicament-filled ampule, located within the syringe barrel, is locked in its pre-injection position so that the syringe is protected against accidental expulsion of the medicament.

It is an object of the present invention to provide an improved disposable hypodermic syringe assembly which is pre-packaged in a pre-injection arrangement with a medicament-filled ampule location within the syringe barrel.

A further object of the invention is to provide an improved disposable hypodermic syringe assembly which is pre-packaged in a pre-injection arrangement with the syringe plunger mounted along the outside of the syringe barrel.

It is a still further object of the invention to provide an improved disposable hypodermic syringe assembly which includes, as a pre-packaged element, a medicament-filled ampule within the syringe barrel with the ampule maintained in a pre-injection position out of fluid communication with the hypodermic needle of the syringe.

Another object of the invention is to provide an improved disposable hypodermic syringe assembly which is pre-packaged in a pre-injection arrangement with the syringe plunger mounted along the outside of the syringe barrel and providing locking means whereby an ampule containing medicament, located within the syringe barrel, is maintained in a pre-injection position in the barrel and out of fluid communication with the hypodermic needle of the syringe.

In accordance with the invention, a one-time use, disposable hypodermic syringe assembly in pre-packaged, pre-injection arrangement is provided which includes as a principal element a molded, plastic syringe barrel with a hypodermic needle mounted in its forward injection delivery end. Preferably the needle is double pointed with a short diaphragm-piercing end projecting into the syringe barrel. The rearward open end of the barrel terminates in a finger engaging flange. Situate within the barrel is a medicament-filled ampule which is sealed at its neckekd-down forward end with a pierceable diaphragm and at its rearward end with a piston-type stopper. The ampule is positioned within the barrel so that its forward diaphragm end is proximate to, or in contact with, but not pierced by the diaphragm piercing end of the needle. Outside of the syringe barrel, and mounted thereon in pre-injection position, is a plunger adapted at one end to interconnect with the piston-type stopper of the ampule and bearing at its other end a finger engaging flanged portion. In the plunger's barrel-mounted, pre-injection and packaged position, the flanged portion of the plunger extends through a forward slot in the syringe barrel and projects inwardly to ingage in locking fashion the necked-down forward end of the medicament-filled ampule to preclude any movement of the ampule within the syringe barrel before the syringe assembly is readied for injection use. The side mounted plunger is maintained in ampule-locking position on the barrel by a removable elastic band surrounding the plunger and barrel elements of the syringe assembly or by wrapping such assembly with a strip of paper that may also contain instructional matter respecting the readying of the syringe assembly for use and cautionary information respecting the medicament contained in the ampule and the indications for its use.

BRIEF DESCRIPTION OF THE DRAWINGS

The accompanying sheets of drawings illustrate practical embodiments of the invention in which.

DESCRIPTION OF THE PREFERRED EMBODIMENTS

Figure 1:
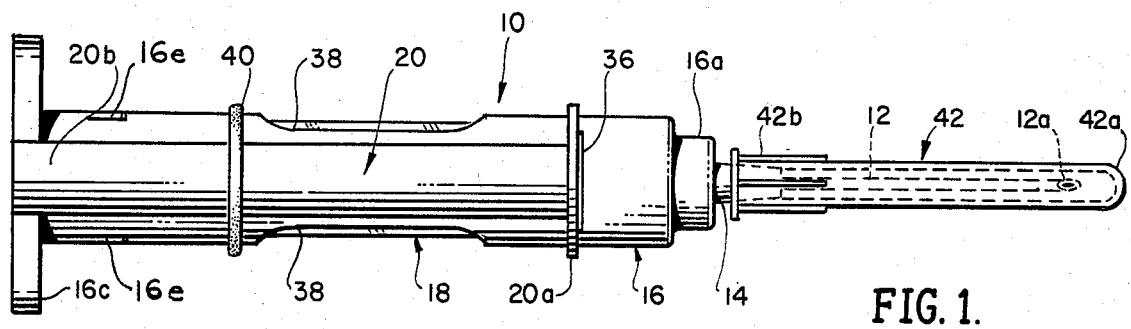
FIG. 1 is a top view of one embodiment of the hypodermic syringe assembly of the present invention in its pre-injection arrangement with the syringe plunger mounted on the syringe barrel in ampule locking position.
Figure 2:
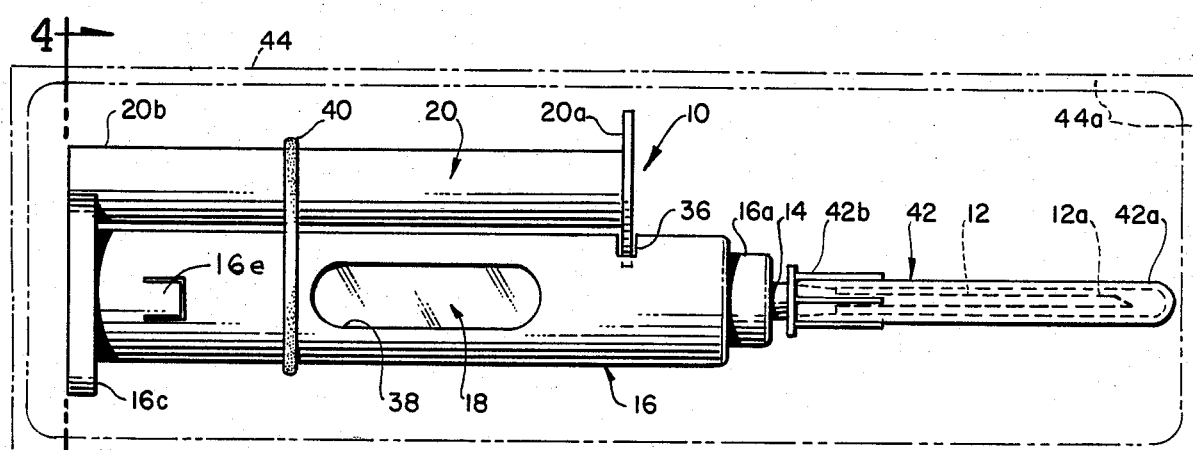
FIG. 2 is a side elevation view of the syringe assembly of FIG. 1.
Figure 3:
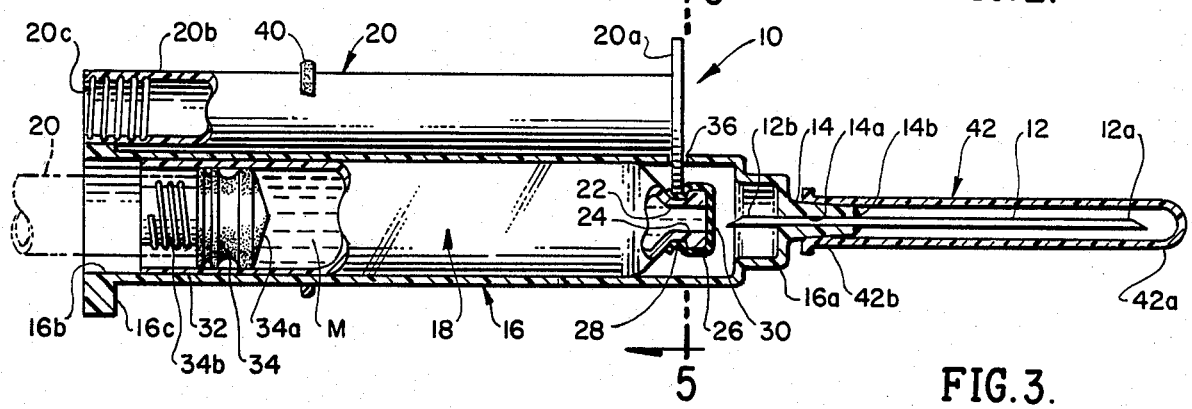
FIG. 3 is a sectioned side elevation view of the syringe assembly of FIG. 1 showing in further partial section the medicament-filled ampule located within the syringe barrel in its locked pre-injection position.

Referring now to the drawings, there is illustrated in FIGS. 1-5 a first preferred embodiment of the improved hypodermic syringe assembly of the present invention in its pre-injection (packaged) arrangement. In FIGS. 1-3 the syringe assembly 10 is shown to comprise principally of a hypodermic needle 12 supported in a needle mounting 14 formed at the forward end of a hypodermic syringe barrel 16. Enclosed within the syringe barrel is a medicament-filled ampule 18 and mounted on the syringe barrel, in its packaged (pre-injection) location is a plunger 20. The hypodermic needle or cannula 12, formed of suitable metal such as stainless steel, has a forward injection end 12a and a rearward projecting diaphragm-piercing end 12b.

The syringe barrel 16 has its forward end closed by end portion 16a which supports the needle mounting 14. At its rearward open end 16b the barrel 16 bears an outwardly extending finger engaging flange 16c. The syringe barrel 16 and needle mounting 14 may be integrally formed from a suitable material, preferably a clear molded thermoplastic material such as polypropylene, nylon, poltystyrene or polyethylene. To securely support the hypodermic needle or cannula 12 in the mounting 14 so as to resist the thrust and tensile forces normally encountered in inserting and withdrawing the needle in making a hypodermic injection, the needle is force fit into the aperature 14a extending through mounting 14 and suitably bonded to such mounting by a resin bonding agent 14b, such as epoxy resin, which has a high bonding affinity for the metal of the needle and the plastic of the mounting.

The medicament-filled ampule 18, as shown, is formed of glass and has a necked-down forward end portion 22 which terminates in opening 24 surrounded by annular bead 26 forming an annular groove 28. The forward end 22 of ampule 18, at opening 24, is closed by a diaphragm cap 30 (of resiliant material such as rubber) which is stretched over opening 24 and grips the necked-down end portion 22 of the ampule via its repose in groove 28. The rearward end 32 of ampule 18 is open for receipt of a piston-type stopper 34 which has a forward medicament-interfacing surface 34a and a rearwardly extending threaded portion 34b for interconnection with plunger 20 when the syringe is readied for use. Medicament fluid M may be introduced to the ampule 18 by any well known means during the separate manufacture of the ampule and filling of same.

The syringe plunger or piston rod 20, as shown in FIG. 3, is hollow and includes a finger (thumb) engaging flange or disc 20a at one end and such plunger has at its opposite end 20b internal threads 20c for interconnection of the plunger with threaded portion 34b of the piston-type stopper 34 of ampule 18. As has been previously indicated, the syringe plunger 20, in its pre-injection arrangement, is mounted on the syringe barrel 16. The finger engaging flange 20a of the plunger extends in radial outwardly fashion from the plunger body 20. With the syringe plunger 20 mounted on the barrel 16 a portion of flange 20a extends through slot 36 in the barrel and in an arcuate notched area 20d of the flange 20a the flange extends into a portion of annular groove 28 of ampule 18 to lock the ampule against forward or rearward movement within syringe barrel 16. The slot 36 in barrel 16 is positioned so that, in its locked position, the diaphragm cap 30 on ampule 18 is in proximity with the diaphragm piercing end 12b of needle 12 but out of contact therewith. The threaded end 20b of the plunger or piston rod 20 rests in an arcuate notch 16d in the finger engaging flange 16c of barrel 16. The syringe plunger 20 may be formed from molded thermoplastic material of the type used for the syringe barrel 16 but such molded material need not result in a clear plastic plunger structure.

As shown in FIGS. 1 and 2, the syringe barrel 16 may be provided with cut-out ports or windows 38 so that clear viewing can be had of the enclosed ampule 18 and its medicament and so that any volume indication lines and numerals on the ampule can be read. The syringe barrel 16 is sized along its length in its internal diameter so that ampule 18 may be easily loaded into the barrel through open end 16b. As the ampule 18 is inserted into barrel 16 it impinges upon one or more lock tabs 16e in the barrel wall. The lock tabs normally project slightly inward of the barrel wall and are forced outwardly to a position flush with said wall by ampule 18 when the latter is in its pre-injection position. With ampule 18 pushed forwardly by plunger 20 to its injection-ready position (with its diaphragm 30 pierced by needle end 12b) the lock tabs 16e snap inwardly past the rearward end 32 of ampule 18 to lock the ampule in its forwardmost position. The plunger 20, in its pre-injection position, may be maintained on syringe barrel 16 through the use of one or more elastic bands 40 or by other appropriate wrapping material. To protect the needle 12 from contamination and physical damage, there is provided a suitable sheath or cap 42. The needle sheath 42 may be molded out of an appropriate thermoplastic material and is provided with a closed forward end 42a and an open rearward end 42b which snugly engages the outer surface of the needle mounting 14.

Figure 4:
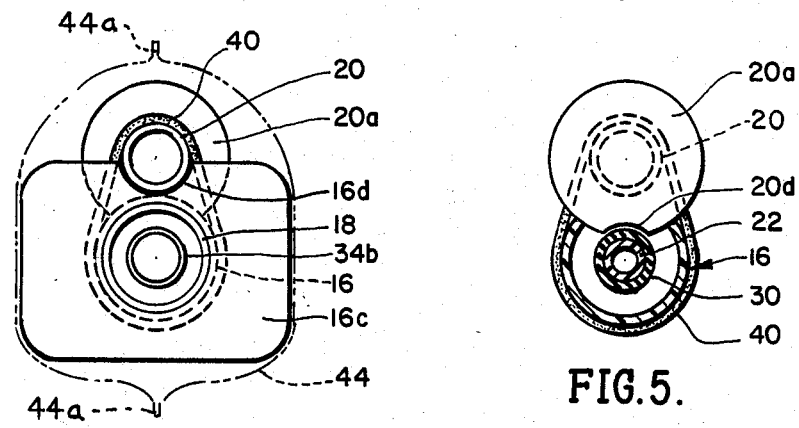
FIG. 4 is an end view of the hypodermic syringe assembly of FIGS. 1 and 2 taken on line 4—4 of FIG. 2.
Figure 5:
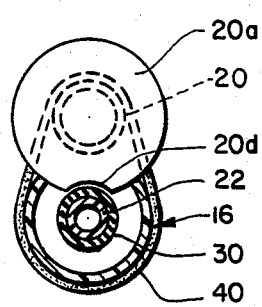
FIG. 5 is an end view of the hypodermic syringe assembly of FIGS. 1 and 2 taken on line 5—5 of FIG. 3.

As shown in FIG. 2, the hypodermic syringe assembly of the invention, in its pre-injection arrangement, may be enclosed in a package 44 of any well known type which permits internal sterilization of the packaging material and the contents of the package. As shown in FIGS. 2 and 4 the package 44 is of film plastic envelope type, heat sealed at its peripheral edges 44a, and may be provided with peel back opening tabs. Alternatively, the syringe assembly may be packaged in a blister type package or other well-known type of package adapted for sterile disposable medical instruments and supplies.

In assembling the hypodermic syringe of the invention in injection-ready arrangement, the plunger 20 is removed from its ampule-locking position along the side.of syringe barrel 16. While grasping the barrel and ampule 18 through side ports 38 to maintain the ampule in its position out of contact with needle end 12b, the end 20b of plunger 20 is threaded onto the threaded portion 34b of the piston-type stopper 34 in the end of ampule 18. With the plunger 20 threaded to stopper 34b the plunger extends rearwardly of the syringe barrel as shown in phantom in FIG. 3. The injection-ready syringe assembly is held by the operator by two fingers engaging barrel flange 16c (one finger or each side of the barrel) with the operator's thumb (same hand) engaging flange 20a of the plunger 20. Thus, when the injection-ready syringe assembly is held as described, the assembly can be easily manipulated to cause the piston or plunger 20 to first move the ampule forwardly within barrel 16 to a position whereat the ampule diaphragm 30 abuts the internal surface of the needle mount 14 with the needle portion 12b having pierced the diaphragm 30 placing the needle in fluid communication with the medicament M within the ampule. Further forward movement by the plunger 20 causes forward movement of the piston-type stopper 34 with the result that medicament is expelled from the ampule through the cannula 12 until it is discharged by the needle end portion 12a. After the discharge of a drop of medicament from the needle point of needle portion 12a (no air remaining in the cannula) the syringe assembly is ready for use in the delivery of medicament to a patient by hypodermic injection.

Figure 6:
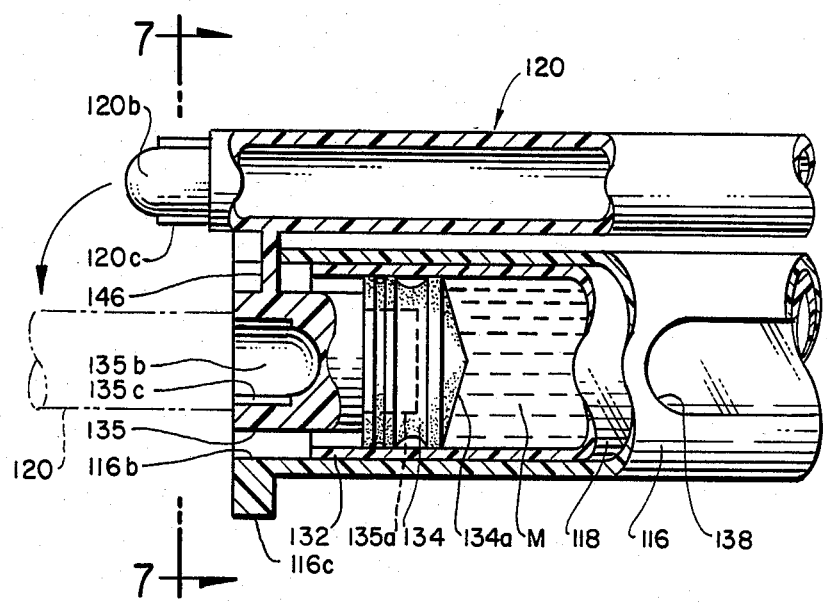
FIG. 6 is an enlarged sectioned partial side elevation view of an alternative embodiment of the hypodermic syringe assembly of the present invention in its pre-injection arrangement.
Figure 7:
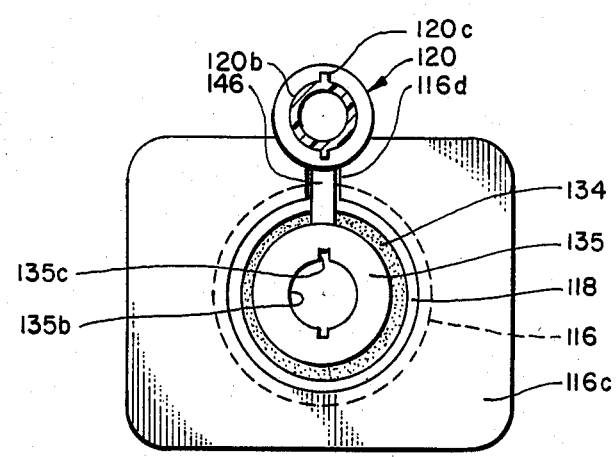
FIG. 7 is an end view of the hypodermic syringe assembly of FIG. 6 taken on line 7—7 of FIG. 6.

A second embodiment of the hypodermic syringe assembly of the present invention, in a pre-injection arrangement, is illustrated in FIGS. 6 and 7. In these figures there is shown a modified means for making the connection between the piston-type stopper of the ampule contained within the syringe barrel of the syringe assembly of the invention and the piston or plunger utilized to actuate such stopper during the making of a hypodermic injection via the assembly. In FIG. 6 syringe barrel 116 encloses medicament-filled ampule 118. The barrel 116 bears at its rearward open end 116b an outwardly extending finger flange 116c. The rearward end of ampule 118 is open for receipt of piston-type stopper 134 which has a forward medicament-interfacing surface 134a.

The syringe plunger or piston rod 120 of FIG. 6 is hollow and has at its rearward end a projecting male portion 120b for interconnection of the plunger with the piston-type stopper 134. To make sure interconnection the stopper is provided with a female plunger connection element 135 which has a portion 135a extending into and affixed to stopper 134 and a cavity 135b for mating with male projecting portion 120b of plunger 120. The cavity 135b of element 135 is provided with one or more keyways 135c which receive keys 120c, borne by projecting portion 120b of plunger 120, to prevent rotation of plunger 120 with respect to stopper 134 when the plunger is in injection position extending rearwardly from such stopper as shown in phantom in FIG. 6.

In the pre-injection syringe assembly embodiment, as illustrated in FIGS. 6 and 7, the plastic plunger connection element 135 of ampule stopper 134 and the palstic plunger 120 are molded together and interconnected by connecting band 146. Connecting band 146 extends between plunger 120 and element 135 through slot 116d in finger engaging flange 116c and is molded to a thickness that permits its flexibility whereby the plunger may be swung or moved to a position for insertion of plunger portion 120b into cavity 135b of connection element 135 of the piston-type stopper 134. As in the syringe assembly embodiment illustrated in FIGS. 1-5, the syringe barrel 116 is provided with ports or windows 138.

The injection-ready hypodermic syringe assembly of the embodiment of the invention as illustrated in FIGS. 6 and 7 is manipulated by the operator in the same manner as previously described with respect to the embodiment of the invention illustrated in FIGS. 1-5.

While preferred embodiments of the invention have been described and illustrated in the foregoing specification and accompanying drawings, it is to be understood that such descriptions and drawings are merely illustrative of the underlying features of the invention and are not to be limiting of the scope of the invention and the following claims.

What I claim is:

1. A one-time-use, disposable hypodermic syringe assembly in medicament-filled, pre-injection arrangement comprising:
   (a) a plastic syringe barrel with a hypodermic needle mounted in its forward injection delivery end, the injection point of said needle projecting outwardly and forwardly of the barrel and the butt end of said needle projecting rearwardly within the barrel;
   (b) a medicament-filled ampule positioned within the syringe barrel, said ampule having a needle-pierceable diaphragm closure at its forward end and a piston-type stopper at its rearward end; and
   (c) a plunger removably seated on the outside of the syringe barrel along the length thereof, said plunger including flange means which during the time that the plunger is seated on the outside of said barrel, locks the medicament-filled ampule at its diaphragm end out of piercing contact with the rearwardly extending butt end of said needle, and said plunger also including means for connecting same with the piston-type stopper of said ampule to render said plunger operable for use in moving said ampule, after removal of the plunger from its ampule-locking position on the syringe barrel, forwardly to effect piercing of said diaphragm by the butt end of said needle and in thereafter moving the piston-type stopper forwardly within said ampule to expel medicament out of said ampule and through said needle for injection purposes.

2. A one-time-use, disposable hypodermic syringe assembly in medicament-filled, pre-injection arrangement as claimed in claim 1 wherein the flange means of said plunger, during the time that the plunger is mounted on the outside of the syringe barrel along the length thereof, extends in part through a slot in said barrel and engages the medicament-filled ampule to provide the means for locking said ampule at its diaphragm end out of diaphragm-piercing contact with the rearwardly extending butt point of said needle.

3. A one-time-use, disposable hypodermic syringe assembly in medicament-filled, pre-injection arrangement as claimed in claim 2 wherein the medicament-filled ampule within the syringe barrel has a necked-down portion at its diaphragm end and the flange means of said plunger, in the part thereof which extends through the slot in said barrel, engages said necked-down portion of said ampule to lock said ampule at its diaphragm end out of diaphragm-piercing contact with the rearwardly extending butt point of said needle.

4. A one-time-use, disposable hypodermic syringe assembly in medicament-filled, pre-injection arrangement as claimed in claim 1 wherein the means for connecting the plunger with the piston-type stopper of the medicament-filled ampule comprises mating threads borne by said plunger at its end opposite the end bearing the flange and by said stopper in a portion extending outwardly of said ampule.

5. A one-time-use, disposable hypodermic syringe assembly in medicament-filled, pre-injection arrangement as claimed in claim 1 wherein the means for connecting the plunger with the piston-type stopper of the medicament-filled ampule comprises a male projection at the end of said plunger opposite the end bearing the flange, said male projection being insertable into a mating female cavity of said stopper.

6. A one-time-use, disposable hypodermic syringe assembly in medicament-filled, pre-injection arrangement comprising:
   (a) a plastic syringe barrel with a double-pointed hypodermic needle mounted in its forward injection delivery end, the injection point of said needle projecting outwardly and forwardly of the barrel and the butt point of said needle projecting rearwardly within the barrel;
   (b) a medicament-filled glass ampule positioned within the syringe barrel, said ampule having a necked-down portion in the area of its forward end and a needle-pierceable diaphragm closure at said forward end, and said ampule having a piston-type stopper at its rearward end; and
   (c) a plastic plunger removably seated on the ouside of the syringe barrel along the length thereof, said plunger including at one end a thumb engaging flange which, during the time that the plunger is mounted on the outside of said barrel, extends in part through a slot in said barrel and engages the medicament-filled ampule to lock said ampule at its diaphragm end out of diaphragm-piercing contact with the rearwardly extending butt point of said needle, and said plunger including means at its end opposite said flange for connecting said plunger to the piston-type stopper of said ampule to render said plunger operable for use in moving said ampule, after removal of the plunger from its ampule-locking position on the syringe barrel, forwardly to effect piercing of said diaphragm by the butt point of said needle and in thereafter moving the piston-type stopper forwardly within said ampule to expel medicament out of said ampule and through said needle for injection purposes.

7. A one-time-use, disposable hypodermic syringe assembly in medicament-filled, pre-injection arrangement as claimed in claim 6 wherein the means for connecting the plunger with the piston-type stopper of the medicament-filled ampule comprises mating threads borne by said plunger at its end opposite the end bearing a thumb engaging flange and by said stopper in a portion extending outwardly of said ampule.

8. A one-time-use disposable hypodermic syringe assembly in medicament-filled, pre-injection arrangement as claimed in claim 6 wherein the piston-type stopper of the medicament-filled ampule includes a rearwardly extending portion having a female cavity and the means for connecting the plastic plunger with said piston-type stopper comprises a male projection at the end of said plunger opposite the end bearing the thumb engaging flange, said male projection mating with and being insertable into the female cavity of the plastic portion of said stopper.

9. A one-time-use, disposable hypodermic syringe assembly in medicament-filled, pre-injection arrangement as claimed in claim 8 wherein the means for connecting the plunger with the piston-type stopper of the medicament-filled ampule further includes a connecting flexible plastic band extending between the plastic portion of said piston-type stopper and said plastic plunger.

10. A one-time-use, disposable hypodermic syringe assembly in medicament-filled, pre-injection arrangement as claimed in claim 6 wherein the plastic syringe barrel bears means for locking the medicament-filled glass ampule in its forwardmost position within the barrel after said ampule has been moved to said position by the plunger with the attendant piercing of the diaphragm closure at the forward end of said ampule by the butt point of the hypodermic needle of said syringe.

11. A one-time-use, disposable hypodermic syringe assembly in medicament-filled, pre-injection arrangement as claimed in claim 10 wherein the means for locking the medicament-filled glass ampule in its forwardmost position within the syringe barrel comprises lock tabs molded into said barrel which snap inwardly past the rearward end of said ampule after said ampule has been moved to its forwardmost position.

* * * * *